United States Patent [19]
Yamaguchi

[11] Patent Number: 5,503,475
[45] Date of Patent: Apr. 2, 1996

[54] METHOD FOR DETERMINING THE CARBON EQUIVALENT, CARBON CONTENT AND SILICON CONTENT OF MOLTEN CAST IRON

[75] Inventor: Takeshi Yamaguchi, Tokyo, Japan

[73] Assignee: Metec Corporation, Tokyo, Japan

[21] Appl. No.: 270,415

[22] Filed: Jul. 5, 1994

Related U.S. Application Data

[63] Continuation of Ser. No. 938,149, Oct. 23, 1992, abandoned.

[51] Int. Cl.$^6$ .......................... G01N 25/02; G01K 13/02; G01K 3/04
[52] U.S. Cl. .......................... 374/26; 374/139; 374/157; 420/28; 420/31; 420/577; 420/579; 420/580
[58] Field of Search ................ 374/26, 139, 157; 73/DIG. 9; 420/577, 579, 580, 31, 28

[56] References Cited

U.S. PATENT DOCUMENTS

| | | | |
|---|---|---|---|
| 2,609,289 | 9/1952 | McKinney et al. | 420/28 |
| 3,267,732 | 8/1966 | Hance | 374/26 |
| 3,546,921 | 12/1970 | Bourke et al. | 374/26 |
| 3,663,212 | 5/1972 | Heine et al. | 420/31 |
| 4,008,604 | 2/1977 | Roach et al. | 420/29 |
| 4,059,996 | 11/1977 | Cure | 374/157 |
| 4,166,738 | 9/1979 | Plessers | 420/31 |
| 4,261,740 | 4/1981 | Plessers | 420/31 |
| 4,515,485 | 5/1985 | Cassidy et al. | 374/157 |

FOREIGN PATENT DOCUMENTS

| | | | |
|---|---|---|---|
| 0208049 | 3/1984 | Germany | 420/28 |
| 54-36797 | 3/1979 | Japan . | |
| 54-11718 | 5/1979 | Japan . | |
| 0092409 | 5/1985 | Japan | 420/31 |
| 0610869 | 6/1978 | U.S.S.R. | 420/31 |
| 0290267 | 6/1929 | United Kingdom | 420/28 |
| 0972708 | 10/1964 | United Kingdom | 420/31 |

*Primary Examiner*—Diego F. F. Gutierrez
*Attorney, Agent, or Firm*—Larson and Taylor

[57] ABSTRACT

In measuring a cooling curve by means of thermal analysis of cast iron, a compressed powder moulding or sintered moulding of tellurium, bismuth, boron, zinc and/or aluminum is fixed to the inner surface of a cooling curve measuring cup, and a melt is poured into said cup when primaly crystalized and eutectic temperatures based on the metastable solidification of iron, cementite and silicon cleary appear. This method allows the carbon equivalent, carbon content and silicon content of the cast iron to be determined and the physical and mechanical properties of the iron to be estimated. Additionally, said compressed metallic powder moulding or sintered moulding is arranged at and fixed to said cooling curve measuring cup used in the method, while enclosing a thermocouple.

5 Claims, 1 Drawing Sheet

METHOD FOR DETERMINING THE CARBON EQUIVALENT, CARBON CONTENT AND SILICON CONTENT OF MOLTEN CAST IRON

This application is a continuation of application Ser. No. 07/938,149 filed Oct. 23, 1992, now abandoned.

TECHNICAL FIELD

This invention relates to methods of accurately measuring a cooling curve of molten cast iron by thermal analysis thereby determining the carbon equivalent, carbon content and silicon content of the iron and estimating the physical and mechanical properties of the iron whereby the furnace front administration of the pre-casting process in the casting factory is sufficiently administered for a cupola and the melt charging from the furnace is measured. The invention also relates to a cooling curve measuring cup used in these methods.

BACKGROUND TECHNIQUE

The principle for the measurement of carbon equivalent involves monitoring a ternary, or a pseudobinary system, comprising the elements of iron, carbon and silicon at the initial thermal arrest temperature (primaly crystal to be liquidus) when the melt of cast iron solidifies to make it carbon equivalent. Though carbon equivalent is expressed in various ways the most general definition is the total percent of carbon plus one-third (Si% plus P%). A further application involved in carbon equivalent measurements are measuring eutectic temperature, interrelating the temperature with liquid, liquid plus solid, and solid determining, the silicon and carbon contents, and estimating the physical and mechanical properties of the cast iron as a function of the time until solidification of the melt. It is known that according to the application, the numerical values thus obtained are corrected and analyzed depending on the modification of practical profile, material and the like of the casting. Further, it is possible to know the state of melt accurately and more quickly and field-like than any other analyzing method by means of a cup which is manufactured by a known technique and pre-arranged before the pouring of the melt to allow the melt to be administered before casting. In case the constituents and various properties of the molten cast iron differ from those intended a suitable pretreatment can be carried out. These known techniques are disclosed in U.S. Pat. No. 3,267,723 and Japanese Patent No. 820,206 based thereon.

Compared with the time when said known techniques were proposed, a wider range of casting materials are available in the present casting industries. High technology has provided compacted graphite iron (so-called CV cast iron) or austempered ductile iron (so-called ADI cast iron) and cast iron alloys have been improved and developed which require an accurate and a quicker technique of administering the in-situ furnace front melt. That is, iron and carbon system is a binary system whereas iron, carbon and silicon system is a ternary system. In the binary system the eutectic temperature is constant whereas in the ternary system it is maximum or minimum, and conditions have become diverse such that cast irons are greatly affected by the silicon content, and according to the additive elements for cast iron alloys the eutectic temperature rises for some elements and is lowered for some others. A further complicated phenomenon is that in the solidification of the basic elements iron, carbon and silicon of ternary system there are two equilibriums of completely stable solidification of iron-carbon (graphite)-silicon system and metastable solidification of iron-carbon (cementite)-silicon system.

Additionally, as the cooling rate changes or the additive elements differ, the two equilibriums alternately occur in the same melt in some occasions. Such a multi-equilibrium problem causes the complication of solidification of cast iron system. Under the existing circumstances where operation by cupola is gradually shifting these days to the melting by electric furnace because of the control to the environmental contamination, serious problems are presented not only to steels but also to cast irons. The problems include not only the characteristic change of the melt caused with time after melting and the simple change of the constituents of the melt but also for the oxygen content, oxide or solved oxygen content in the melt.

This makes known thermal analysis methods unsatisfactory. It is therefore necessary to accurately measure not only the primarily crystallized temperature but also the eutectic temperature. Thus, in order to measure the cooling curve in a safe white pig iron state (iron and cementite system), it is necessary to measure the semi-stable solidification as a requisite condition, not only for the cooling curve, but also for samples for mechanical analysis such as in emission spectrum analysis method, X-ray analysis method or the like.

The inventor of this invention has performed extensive research in an attempt to solve the above problems. Known methods of adding graphitization-hindering elements such as tellurium, bismuth and boron as metastable solidification promoters according to prior art include one of adding, as a paint for chill wash or the like, metal tellurium powder or the like in a measuring cup. This method is based on the above-referred patent inventions. However, it is questionable in those inventions whether said elements are always accurately added in a constant proportion, and it is doubtful whether correct primaly crystallized and eutectic temperatures are always obtained from the samples of melts of cast irons. Referring to a method of obtaining a cooling curve, Japanese Patent No. 820,206 describes in its claims the addition of bismuth, boron, cerium, lead, magnesium and tellurium, and compounds and mixtures thereof into the melt as stabilizer. However, cerium and magnesium are spherification reaction agents and spherification stabilizers for typical ductile cast irons, and they disturb the equilibrium state of metal-stable solidification of iron-cementite systems necessary to make the measurement of respective primaly crystallized and eutectic temperatures. It is naturally not until the measurement of the equilibrium state that the primaly crystallized and eutectic temperatures are measured. Cerium and magnesium necessarily pass through deoxidation, desulfuration and decarburization processes before the spherification of graphite, and it will be clear it is inconvenient to use elements which obtain a decarburization action, in measuring the carbon equivalent and carbon content.

DISCLOSURE OF THE INVENTION

In the present invention various studies and experiments have been carried out to eliminate the above drawbacks of the known techniques. The technical constitution of the invention lies in a method of measuring a cooling curve by means of thermal analysis of molten cast iron. According to the method, a compressed powder molding or sintered molding prepared of a metallic powdery body of tellurium, bismuth, boron, zinc or aluminium or a mixture thereof is fixed to the inner surface of a cooling curve measuring cup, a melt of cast iron is then poured into said measuring cup. When primaly crystallized and eutectic temperatures based on the metastable solidification of iron, cementite and silicon clearly appear on the cooling curve of the cast iron, the carbon equivalent, carbon content and silicon content of the iron are determined and also the physical and mechanical properties thereof are estimated. The present invention also relates to a cooling curve measuring cup for thermal analysis of cast iron, wherein a compressed metallic powder molding or sintered molding of tellurium, bismuth, boron, zinc or aluminum or a mixture thereof is arranged at and fixed onto the inner bottom surface of said cup, while enclosing a thermocouple.

As described above, in view of the fact that a sufficient deoxidative effect is produced if used even in a small amount and the primaly crystallized and eutectic temperature of cast iron are not adversely affected even for an alloy element, the inventor of this invention has focused on aluminium. He has also noticed that by adding a small amount of zinc to enhance the effect of the metastable solidification promoters such as tellurium, bismuth and boron and to control a little exothermic phenomenon which occurs due to the deoxidation reaction of aluminium it is possible to cancel the heat generation by the evaporation latent heat to allow the effect of the metastable solidification to be improved. It is also possible to completely remove the affection caused by the oxide or solved oxygen content. According to the invention, therefore, a powdery body of tellurium, bismuth or boron is mixed with that of tellurium, the mixture is formed as a compressed powder molding which is fixed to the inside of the cooling curve measuring cup. The mixture as a molding reacts with the pouring melt of the cast iron to improve the melt so that it is possible to quickly and accurately measure the carbon equivalent, carbon content and silicon content of the iron and to determine the physical and mechanical properties of the cast iron.

BEST EMBODIMENT FOR CARRYING OUT THE INVENTION

Figure 1:
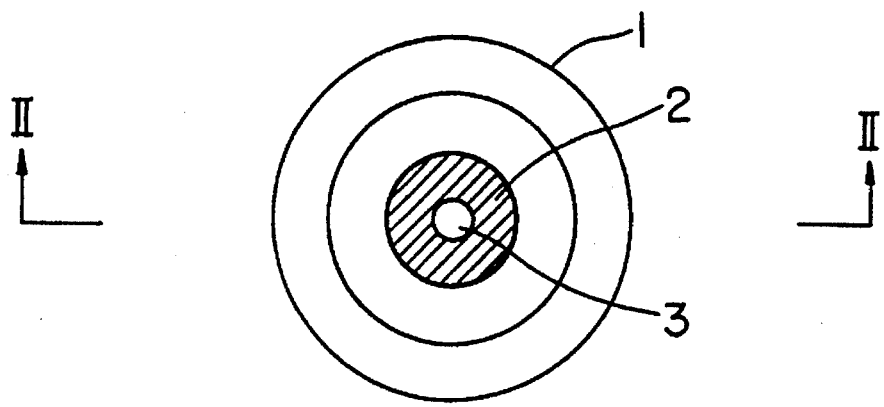
FIG. 1 is a plan view of a cooling curve measuring cup of the invention.
Figure 2:
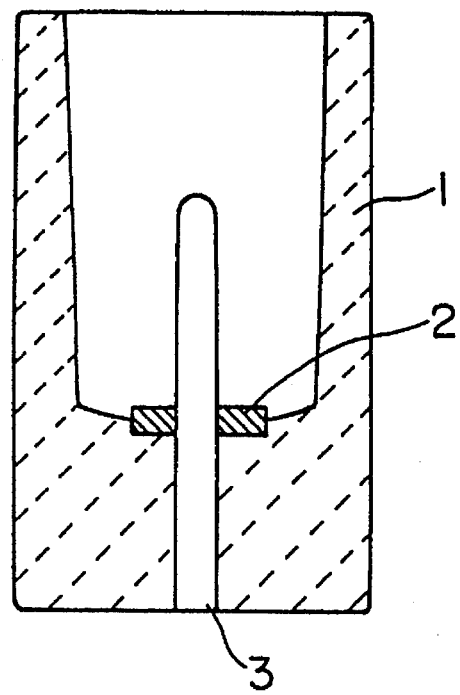
FIG. 2 is a vertical sectional view taken along the line II—II of FIG. 1.

The method of the invention has been carried out by using a cooling curve measuring cup (1) shown in FIGS. 1 and 2. A ring-like molding (2) of the invention is arranged at the bottom surface within said cup (1) and encloses a thermocouple (3). The thermocouple senses the temperature of a cast iron melt inside the cup (1). A cooling curve is obtained by plotting temperature as a function of time as the melt cools. Primaly crystallized and eutectic temperatures may then be obtained from the cooling curve. Said molding (2) is prepared in such a manner that metallic powder of tellurium, bismuth, boron, zinc or aluminium or a powdery mixture thereof is compressed or sintered for molding. A suitable composition thereof may be in the following range because of the above reasons:

| Aluminium | 3–20% by weight |
| Zinc | 3–20% by weight |
| Tellurium | The balance |

Further bismuth and boron can be substituted for part of said tellurium content up to 50% by weight.

It has been confirmed from the result of experiments that with a composition less than the above range it is incapable achieving the desired object of the invention while an additive amount exceeding the upper limit is no more than a waste of expensive elements.

Additionally, the arrangement of the molding (2) within the measuring cup, which is shown in the drawings, just shows the best embodiment, and the arrangement is not restricted to the one as shown in the drawings.

EXAMPLE 1

Molding composition

| Aluminium | 7.3% by weight |
| Zinc | 9.7% by weight |
| Tellurium | The balance |

Conditions for molding compressed powder:

A powdery body of said composition was uniformly mixed, the mixed powder was charged in a powder metallurgical die having a desired size, and it was molded to be a ring-like molding of about 1 mm thickness by a powder metallurgical press. In the preparation of such a molding, binder is not used at all for the powdery body, but it is not a hindrance to employ a small amount of a volatile binder according to the mixing proportion of the powder. As shown in FIG. 2, a ring-like molding thus prepared is pressed-in to the bottom center of a measuring cup manufactured by shell molding sand while making a pocket suited to the outside diameter and thickness of the molding so as to be fixed there. The inside diameter of the molding is made a little large than the outside diameter of a thermocouple protective pipe to avoid problems in inserting the thermocouple. Samples of cast irons to be measured, in various compositions, being at 1400°–1405° C., were poured into the cups, and the following result was obtained.

|  | Hypo-eutectic cast iron | | Hyper-eutectic cast iron | |
| --- | --- | --- | --- | --- |
|  | (1) | (2) | (1) | (2) |
| Proeutectic temperature | 1,169° C. (2,136° F.) | 1,154° C. (2,110° F.) | 1,131.5° C. (2,069° F.) | 1,111.5° C. (2,033° F.) |
| Eutectic temperature | 1,115° C. (2,039° F.) | 1,116° C. (2,041° F.) | 1,112.5° C. (2,035° F.) | 1,107° C. (2,025° F.) |
| Carbon equivalent | 4.17 | 4.30 | 4.48 | 4.71 |
| Carbon content | 3.52 | 3.66 | 3.78 | 3.91 |
| Silicon content | 1.94 | 1.89 | 2.08 | 2.39 |

EXAMPLE 2

| Aluminium | 6.94% by weight |
| Zinc | 9.7% by weight |
| Bismuth | 10.5% by weight |
| Tellurium | The balance |

A mixture of the above constituents was molded in the same manner as in Example 1, and the same operation was affected by using the molding. A result almost the same as in Example 1 was obtained.

The function and effect of the present invention are as follows:

(1) Measurement can be made in a broad range from hypo-eutectic side to hyper-eutectic side and even to cast iron alloys.

(2) Different from conventional methods of coating chill wash or metallic powder of tellurium or the like to the inner surface of a measuring cup it is possible to correctly add a binder of predetermined composition. Unlike chill wash, cooling i.e. so-called recalescence often does not appear on the cooling curve, being sometimes great and sometimes small in the tellurium content in the respective measuring cups. Said recalescence causes the measurement to be difficult. Due to the development of the compound binder it is capable of positively grasping the lower limit value of ternary eutectic temperature so that the stable primaly crystallized and eutectic temperatures in the metastable solidification region of iron-cementite system are always known.

(3) As a result, according to the invention, it is possible to achieve sufficient results with only the additive amount 0.2–1.0% by weight of said compressed powder molding or sintered molding to said cast iron. As a result, it is possible to make an accurate measurement almost by 100% within the ranges of ±0.05% for carbon equivalent, ±0.05% for carbon content and ±0.15% even for silicon content. This demonstrates the ability of the cup as a tool for administering the furnace front melt in a casting factory, and the invention will contribute to management of melting working to cope with advance and development of future casting technology.

INDUSTRIALLY POSSIBLE APPLICATION

According to the present invention, a cooling curve can be accurately measured by thermal analysis of cast iron to determine the carbon equivalent, carbon content and silicon content in the iron and to estimate the physical and mechanical properties of the iron whereby the furnace front administration of the pre-casting processes in a casting factory is easily effected. Additionally, an effective analyzing means in field is provided for distribution and delivery of the melt for from a blast furnace and for sorting of steel making pig iron and various kinds of pig irons for casting.

I claim:

1. In a method of determining the carbon equivalent, carbon content, and silicon content of a molten cast iron by analysis of a cooling curve of a sample of the molten cast iron which comprises:

providing a sample of a molten cast iron in a cooling curve measuring cup, said cooling curve measuring cup containing particulate tellurium in an amount sufficient to promote metastable solidification of the melt in the cup;

cooling the melt sufficiently to solidify the melt in the cup;

measuring the temperature of the melt as it cools to obtain a cooling curve; and determining, by analysis of the cooling curve, the carbon equivalent, carbon content and silicon content of the molten cast iron;

the improvement wherein the tellurium is provided in the cup in the form of a compressed powder molding or sintered powdered molding comprising 3–20 weight % aluminum, 3–20% weight % zinc, and at least 50 weight % of the balance thereof being said tellurium.

2. An improved method according to claim 1 wherein the balance of said molding further comprises at least one member selected from the group consisting of bismuth and boron.

3. An improved method according to claim 1 wherein the amount of said molding is from 0.2 to 1% by weight based on the weight of said sample.

4. An improved method according to claim 1 wherein the balance of said molding consists essentially of tellurium.

5. An improved method according to claim 1 wherein the balance of said molding consists essentially of tellurium and at least one member selected from the group consisting of bismuth and boron.

* * * * *